(12) United States Patent
Poucher (10) Patent No.: US 9,844,393 B2
(45) Date of Patent: *Dec. 19, 2017

(54) METHOD OF IMPLANTING A PENILE PROSTHETIC

(71) Applicant: Coloplast A/S, Humlebaek (DK)

(72) Inventor: Neal Poucher, North Oaks, MN (US)

(73) Assignee: Coloplast A/S, Humlebaek (DK)

(*) Notice: Subject to any disclaimer, the term of this patent is extended or adjusted under 35 U.S.C. 154(b) by 0 days.

This patent is subject to a terminal disclaimer.

(21) Appl. No.: 15/286,570

(22) Filed: Oct. 6, 2016

(65) Prior Publication Data

US 2017/0079682 A1 Mar. 23, 2017

Related U.S. Application Data

(63) Continuation of application No. 14/454,732, filed on Aug. 8, 2014, now Pat. No. 9,486,231.

(51) Int. Cl.
| | |
|---|---|
| *A61F 5/00* | (2006.01) |
| *A61B 17/34* | (2006.01) |
| *A61F 2/26* | (2006.01) |
| *A61B 17/28* | (2006.01) |
| *A61B 17/02* | (2006.01) |

(52) U.S. Cl.
CPC .......... *A61B 17/3468* (2013.01); *A61B 17/02* (2013.01); *A61B 17/282* (2013.01); *A61B 17/2816* (2013.01); *A61B 17/2841* (2013.01); *A61B 17/34* (2013.01); *A61F 2/26* (2013.01); *A61F 2250/0003* (2013.01)

(58) Field of Classification Search
CPC ........ A61F 2/26; A61F 5/41; A61F 2005/415; A61B 17/282; A61B 17/2841; A61B 17/2816
USPC ...................................... 600/38–41
See application file for complete search history.

(56) References Cited

U.S. PATENT DOCUMENTS

| | | | |
|---|---|---|---|
| 4,049,002 | A | 9/1977 | Kletschka et al. |
| 4,919,152 | A | 4/1990 | Ger |
| 9,486,231 | B2 * | 11/2016 | Poucher ............ A61B 17/2816 |
| 2001/0005787 | A1 | 6/2001 | Oz et al. |
| 2016/0038288 | A1 | 2/2016 | Poucher |
| 2016/0067045 | A1 | 3/2016 | Daniel |
| 2016/0089240 | A1 | 3/2016 | Daniel |

OTHER PUBLICATIONS

Office Action dated Jan. 3, 2017 in U.S. Appl. No. 14/482,640.

* cited by examiner

*Primary Examiner* — John Lacyk
(74) *Attorney, Agent, or Firm* — Coloplast Corp., Coloplast A/S; Nick Baumann

(57) ABSTRACT

A method of implanting a penile prosthetic includes providing a tool having a barrel and a clasp. The barrel has a curved exterior perimeter and the clasp has a distal end that is free to move away from and towards the barrel. The method includes securing a first lateral edge of a deflated penile implant between the interior surface of the clasp and the curved exterior perimeter of the barrel and securing a second lateral edge of the deflated penile implant between the interior surface of the clasp and the curved exterior perimeter of the barrel, and placing the barrel of the tool and the deflated penile implant into a corpora cavernosum of a penis.

13 Claims, 8 Drawing Sheets

METHOD OF IMPLANTING A PENILE PROSTHETIC

BACKGROUND

An implanted penile prosthetic has proven useful in treating erectile dysfunction in men. The penile prosthetic includes two inflatable cylinders implanted in the penis, a pump implanted in the scrotum or other internal space, and a liquid holding reservoir implanted in the abdomen or other internal space.

In a typical implantation procedure, the penis of the patient is incised in a corporotomy to expose a pair of corpora cavernosa that are aligned axially in a side-by-side orientation within the penis. A cutting implement, such as a curved Mayo scissors, is employed to penetrate the fascia of the penis and form an opening accessing each corpora cavernosum. Subsequently, each corpora cavernosum is dilated (opened) with an appropriate dilation tool to form a recess that is sized to receive one of the two cylinders of the penile prosthetic. Thereafter, a tool (e.g., a "Furlow" introducer) is inserted into each dilated corpora cavernosum to measure a length of the penis distally and proximally to determine a desired length of the cylinders. A cylinder of the appropriately selected length is secured to a suture, and the suture is secured to a needle (sometimes called a "Keith" needle) that is loaded into the Furlow introducer. The Furlow introducer delivers the needle through the dilated corpora cavernosum and out the glans penis. The needle is discarded and the suture is employed to tow the cylinder into place within the dilated corpora cavernosum.

The above-described procedure has proven effective when implanting penile prostheses. However, surgeons and users would both appreciate improved tools for implanting penile prosthetic cylinders.

SUMMARY

One aspect provides a tool for implanting an inflatable penile prosthetic cylinder. The tool includes a barrel and a clasp. The barrel extends from a proximal end to a distal end and has a solid central portion bounded by a curved exterior perimeter of the barrel. The clasp has a proximal end that is attached to the tool and a distal end that is free to move away from and towards the barrel. The clasp has an interior surface located adjacent to the curved exterior perimeter of the barrel and an exposed exterior surface opposite of the interior surface. The interior surface of the clasp is spaced a distance away from the barrel at locations between the proximal end and the distal end of the clasp. The interior surface of the clasp touches the barrel at the distal end of the clasp.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 1A is an exploded side view of a prior art tool for implanting a cylinder into a penis as illustrated in cross-section in FIG. 1B.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the attached claims.

The features of the various exemplary embodiments described in this application may be combined with each other ("mixed and matched"), unless specifically noted otherwise.

End means endmost. A distal end is the furthest endmost location of a distal portion of a thing being described, whereas a proximal end is the nearest endmost location of a proximal portion of the thing being described. The portion next to or adjacent to an end is an end portion.

The term "hemisphere" in this application means one equatorial half of a sphere.

An implantable penile prosthetic system includes two cylinders implanted in the penis, a pump implanted in the scrotum or other internal space, and a liquid holding reservoir implanted in the abdomen or other internal space. The surgeon usually implants the reservoir last, after confirming that the tubing attached to the reservoir, pump, and cylinders is not leaking. The reservoir is filled with saline or another liquid at approximately atmospheric pressure. The pump is employed to transfer the liquid from the reservoir to the cylinders, and in so doing, the liquid in the cylinders is pressurized to create an erection. A flow path is provided to depressurize and return the liquid from the cylinders back to the reservoir.

Figures 1A, 1B:
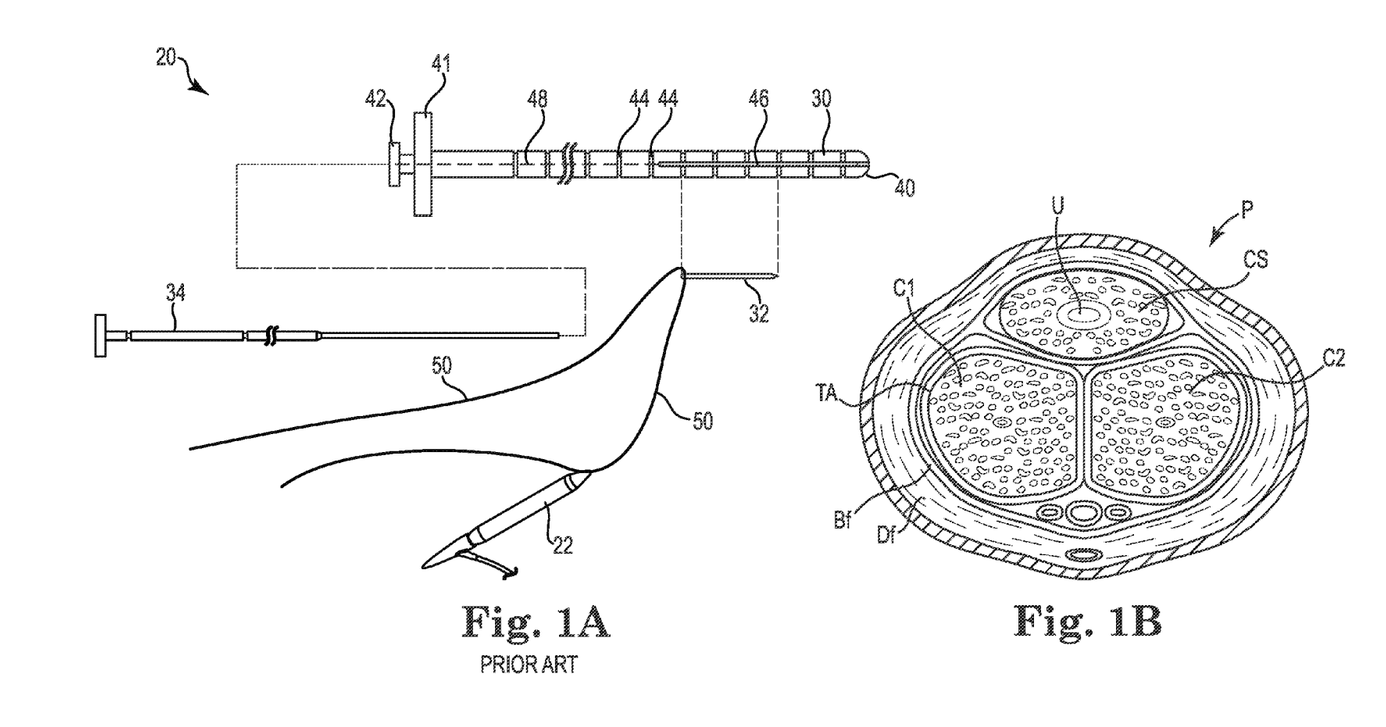

FIG. 1A is an exploded side view of a prior art tool 20 for implanting an inflatable cylinder 22 into a penis P illustrated in FIG. 1B. The inflatable cylinders 22 are fabricated to be pliant and comfortable when deflated and rigid and erect when inflated. The deflated cylinder 22 lacks column strength and will bend and twist and resist being pushed into the penis P. For this reason, a suture or strand is employed to pull the inflatable cylinder into place within the penis P.

The tool 20 includes a barrel 30, a needle 32 that is insertable into the barrel 30, and a plunger 34 that is insertable into the barrel 30 to push the needle 32 out of the barrel 30. One such needle 32 is a Keith needle.

The barrel 30 extends between a curved distal end 40 and a handle 41 provided at a proximal end 42. The barrel 30 has markings 44 applied on an external surface to indicate or measure a depth to which the barrel 30 has been inserted into the corpora cavernosum. The barrel 30 is provided with a slot 46 that is sized to receive the needle 32 and a lumen 48 sized to receive the needle 32 and the plunger 34.

The needle 32 is attached to a tow suture 50 that is coupled with the cylinder 22. The tow suture 50 is generally inserted through an eyelet of the needle 50 and a hole provided at a distal end of the cylinder 22.

The plunger 34 is insertable into the lumen 48 at the proximal end 42 of the barrel 30 and operates to push the needle 32 out of the lumen 48.

FIG. 1B is a cross-sectional view of the penis P oriented to access by the surgeon. The surgeon gains access to the corpora cavernosa though small incisions made through the fascia after the penis is reclined toward the abdomen, as illustrated in the cross-sectional view of FIG. 1B. In the view of FIG. 1B the penis P of the patient is reclined against the torso such that the urethra U, surrounded by corpus spongiosum CS tissue, is oriented upward.

In preparation for the implantation of the penile prosthesis, the groin area of the patient is shaved, cleaned and suitably prepped with a surgical solution prior to draping with a sterile drape as directed by the healthcare provider's procedures. A retraction device, such as a retractor sold under the trademark Lone Star and available from Lone Star Medical Products of Stafford, Tex., is placed around the penis P. A catheter is inserted into the urethra U from the distal end of the penis P into the bladder. Thereafter, the surgeon forms an incision to access the corpora cavernosa C1 and C2 of the penis.

Suitable examples of incisions include either an infrapubic incision or a transverse scrotal incision. The infrapubic incision is initiated between the umbilicus and the penis (i.e., above the penis), whereas the transverse scrotal incision is made across an upper portion of the patient's scrotum.

In the transverse scrotal approach the surgeon forms a 2-3 cm transverse incision through the subcutaneous tissue of the median raphe of the upper scrotum and dissects down through the Darto's fascia Df and Buck's fascia Bf to expose the tunicae albuginea TA of the penis P. Thereafter, each corpora cavernosum C1 and C2 is exposed in a corporotomy where a small (approximately 1.5 cm) incision is formed to allow the surgeon to access to the corpora cavernosa C1 and C2.

Each corpora cavernosum C1, C2 is dilated with an appropriate dilation tool to form a recess in the penis P that is sized to receive one of the two cylinders 22. The barrel 30 of the tool 20 is inserted into each dilated corpora cavernosum C1, C2 to measure the length of the corpora prior to selecting an appropriately sized cylinder 22. The barrel 30 is removed from the penis P. The suture 50 is inserted through the distal, leading end of the cylinder 22 and the needle 32. The needle 32 is loaded into the barrel 30 through the slot 46 and the plunger 34 is inserted into the lumen 48 via the proximal end 42 of the barrel 30. The barrel 30 is inserted into the dilated corpora cavernosum and the plunger 34 is pushed into the lumen 48 to push the needle 32 out of the barrel 30 and through the glans penis. The surgeon captures the needle 32, disengages the needle 32 from the tow suture 50, and pulls on the tow suture 50 to draw the cylinder 22 into the dilated corpora cavernosum. The tow suture 50 is disengaged from the cylinder, which is now implanted within the corpora cavernosum C1 or C2.

Pushing the needle 32 through the glans penis can cause bleeding from the head of the penis, which while harmless, can be alarming to the patient. Surgeons have expressed a desire to avoid the use of the needle 32.

As noted above, the suture 50 is inserted through the distal, leading end of the cylinder 22. The distal end of the cylinder 22 is oftentimes structurally reinforced to accommodate the hole that the suture 50 is passed through. The reinforced end of the cylinder can be felt by some patients who perceive it as a hard and unnatural, undesirable pointed projection.

Embodiments provide a tool for implanting a prosthetic cylinder of such a system into a penis, where the tool does away with the handling and the use of a Keith needle. The tool is useful for measuring the depth of the corpora cavernosum in selecting a length of an appropriately sized cylinder, and then can be used to push the deflated prosthetic cylinder into the opening formed in the penis. The tool may be fabricated from plastic or metal and can be provided in both disposable and reusable forms.

Figure 2:
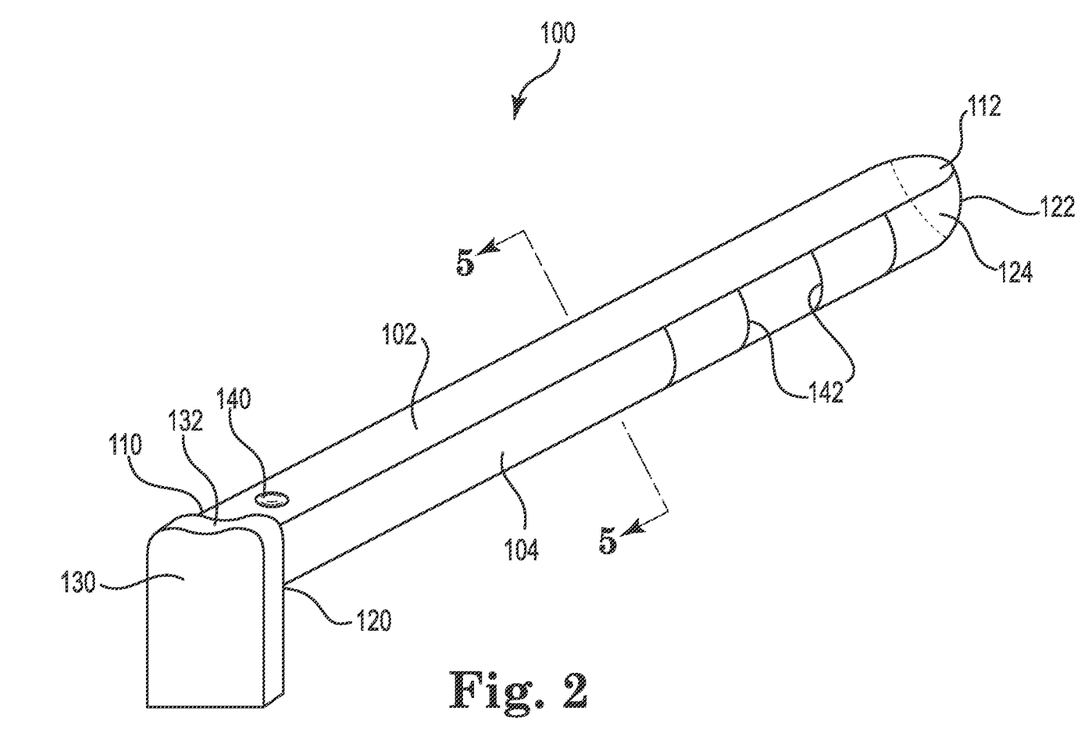
FIG. 2 is a perspective view of one embodiment of a tool for implanting an inflatable penile prosthetic cylinder.
Figure 3A:
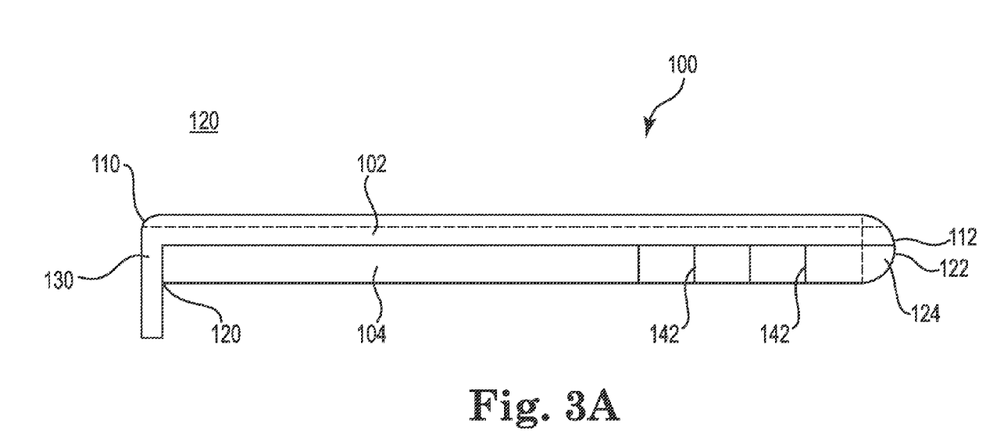
FIGS. 3A and 3B are side views of the tool illustrated in FIG. 2.
Figure 3B:
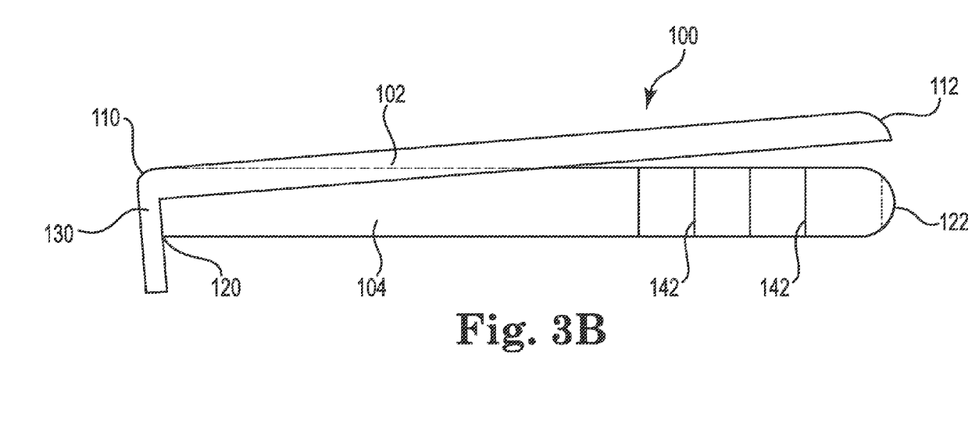
Figure 4:
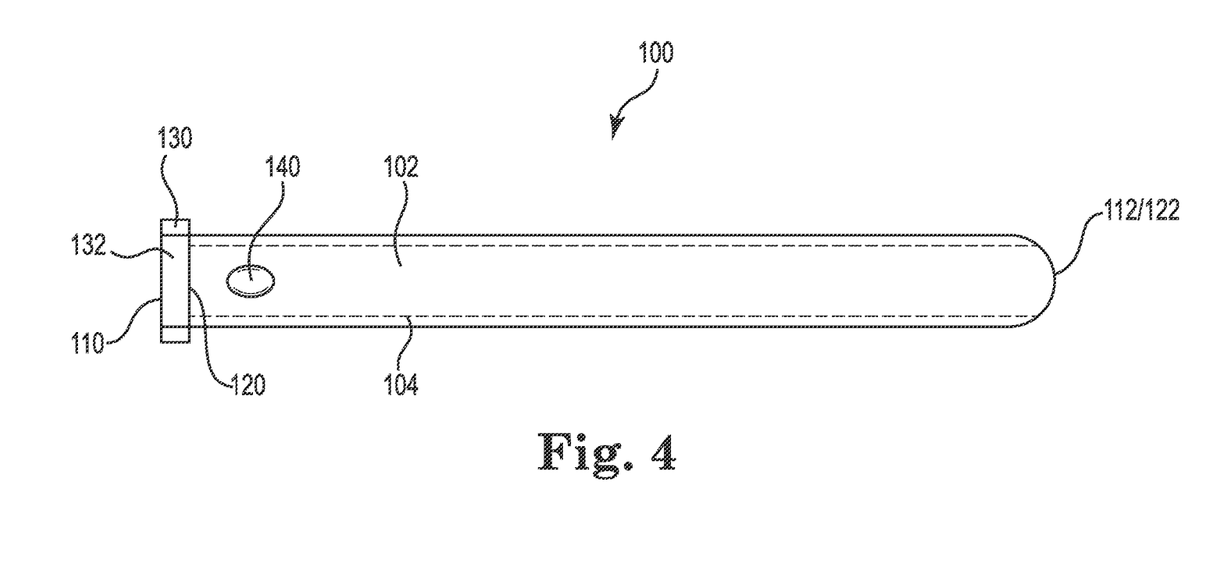
FIG. 4 is a top view of the tool illustrated in FIG. 2.

FIG. 2 is a perspective view, FIGS. 3A and 3B are side views, and FIG. 4 is a top view of one embodiment of a tool 100 useful for implanting an inflatable penile prosthetic cylinder.

The tool 100, as described below, includes a barrel extending from a proximal end to a distal end, the barrel having a solid central portion bounded by a curved exterior perimeter of the barrel; a clasp having a proximal end that is attached to the tool and a distal end that is free to move away from and towards the barrel, where the clasp has an interior surface located adjacent to the curved exterior perimeter of the barrel and an exposed exterior surface opposite of the interior surface; the interior surface of the clasp is spaced a distance away from the barrel at locations between the proximal end and the distal end of the clasp; and the interior surface of the clasp touches the barrel at the distal end of the clasp.

The tool 100 includes a clasp 102 attached to a barrel 104. The clasp 102 extends from a proximal end 110 to a distal end 112, and the barrel 104 extends from a proximal end 120 to a distal end 122. The proximal end 110 of the clasp 102 is connected to either a handle provided with the tool 100 or to the barrel 104.

In one embodiment, the proximal end 110 of the clasp 102 is integrated to the proximal end 120 of the barrel 104. Alternatively, a handle 130 is provided attached to the barrel 104 and the proximal end 110 of the clasp 102 is integrated to the handle 130.

The distal end 112 of the clasp 102 and the distal end 122 of the barrel 104 combine to provide a blunt end surface 124 that is configured to cooperate with the glans penis when the tool 100 is inserted into the corpora cavernosum. One suitable end surface shape is a blunt hemispherical end surface 124.

FIGS. 3A and 3B are side views illustrating that the distal end 112 of the clasp 102 is free to move away from and towards the barrel 104. For example, the clasp 102 is flexible and movable and can be lifted away from barrel 104 to receive portions of a deflated prosthetic cylinder. In one embodiment, a pad 140 is provided on a top exterior surface of the clasp and operates to allow the surgeon to pinch the flexible clasp 102 against the prosthetic cylinder that is captured or clamped between the clasp 102 and the barrel 104 during an implantation procedure.

In one embodiment, the proximal end 110 of the clasp 102 is integrated to the handle 130 and the clasp 102 is pre-stressed such that the distal end 112 of the clasp 102 is forced into contact against the distal end 122 of the barrel 104 until selectively displaced by the surgeon when loading the cylinder into the tool 100. This pre-stressed force fabricated into the clasp 102 allows the clasp 102 to securely capture a portion of the cylinder of the prosthetic device to the tool 100 prior to implantation of the cylinder into the penis.

In one embodiment, the handle 130 is attached to the proximal end 120 of the barrel 104. The handle 130 provides a control surface for the surgeon to control the tool 100 during implantation of a prosthetic cylinder. In one embodiment, the handle 130 includes a concave indent 132 that is sized and configured to provide clearance to receive a surface of the surgeon's thumb or finger.

The clasp 102 is at least as long as the barrel 104, and in the case where the clasp 102 is integrated to the handle 130, the clasp 102 is longer than the barrel 104. A proximal end portion of the clasp 102 is provided with the pad 140 that allows the surgeon to apply downward pressure to further clamp the clasp 102 against the barrel 104.

Embodiments provide demarcations or markings 142, similar to a ruler, applied at least to the barrel 104. The markings 142 are useful in measuring the depth that the tool 100 is inserted into the penis. The markings 142 assist in selecting a prosthetic cylinder with an appropriate length for the patient. The markings 142 include printed indicia or indicia engraved into a surface of the barrel.

Penile prosthetic cylinders are provided in a range of sizes from 12 cm to 20 cm, and the length of the tool is selected to accommodate such cylinders. The tool 100 is suitable fabricated from metal such as stainless steel, or of plastic such as polypropylene or nylon or polyurethane. When fabricated from metal, the clasp 102 is hinged to the barrel 104 or the handle 130. When fabricated from plastic, the clasp 102 is integrated to the barrel 104 or the handle 130 and flexes relative to these components in the form of a living hinge.

Figure 5:
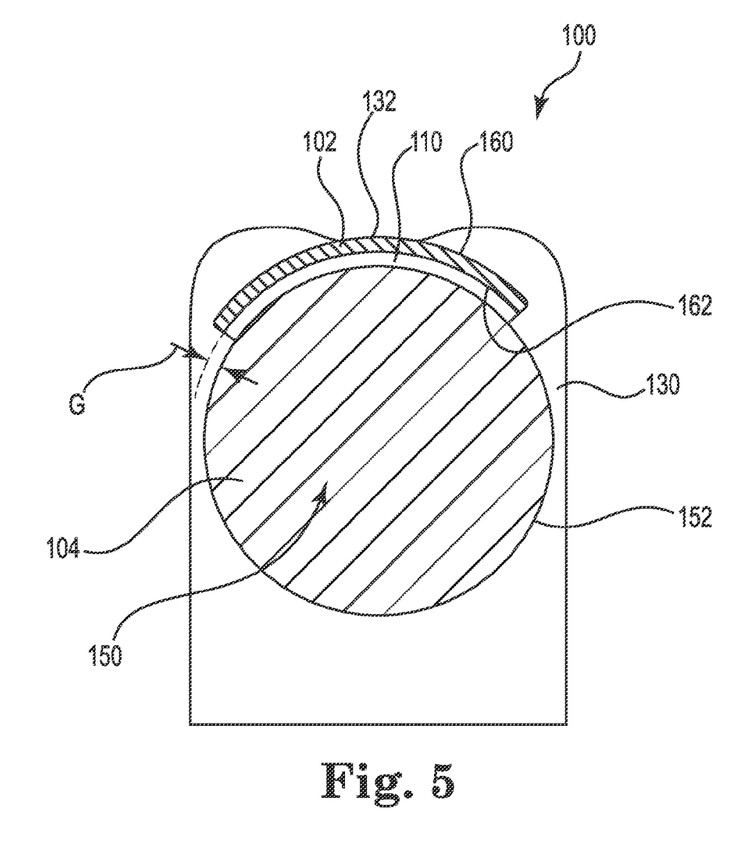
FIG. 5 is a cross-sectional view of the tool illustrated in FIG. 2.

FIG. 5 is a cross-sectional view of a central region of the tool 100 looking toward the handle 130. The barrel 104 has a solid central portion 150 surrounded by a curved exterior perimeter 152. The clasp 102 has an exterior surface 160 and an interior surface 162 that is adjacent to the curved exterior perimeter 152 of the barrel 104.

In one embodiment, the interior surface 162 of the clasp 102 is curved and is parallel to the curved exterior perimeter 152 of the barrel 104. In this sense, the curvature of the interior surface 162 of the clasp 102 is the same or substantially similar to the curvature of the curved exterior perimeter 152 of the barrel 104.

The clasp 102, between its proximal end 110 and distal end 112, is offset distance away from barrel 104 by a gap distance G. In some embodiments the clasp 102 is connected at its proximal end 110 to the handle 130 or the barrel 104, and the distal end 112 of the clasp 102 is stressed to bend into contact with the distal end 122 of the barrel 104. The interior surface 162 of the clasp 102 is spaced a distance away from the barrel 104 at locations between the proximal end 110 and the distal end 112 of the clasp 102. The interior surface 162 of the clasp 102 touches the barrel 104 at the distal end 112 of the clasp 102. The gap G is provided to receive a portion of the deflated cylinder that is insertable between the clasp 102 and the barrel 104.

Figure 6:
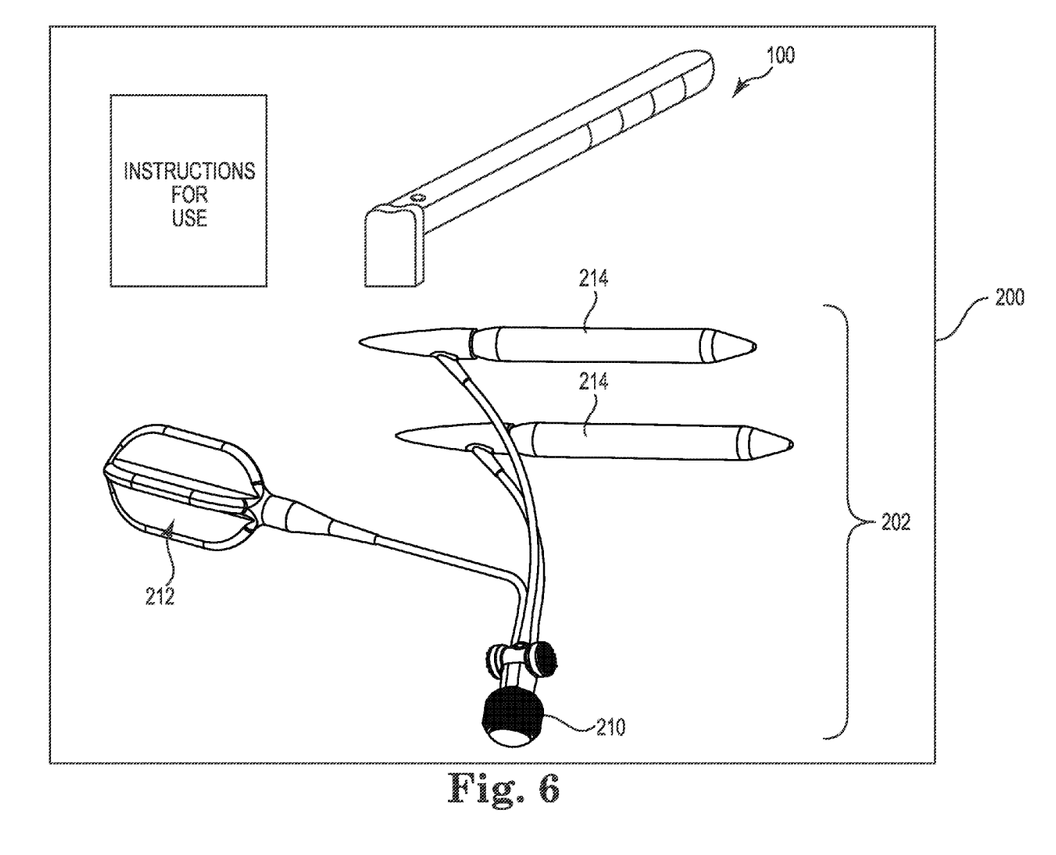
FIG. 6 is a schematic view of a kit of parts including an implantable penile prosthetic system and the tool illustrated in FIG. 2.

FIG. 6 is a schematic view of a kit of parts 200. The kit of parts includes the tool 100, an implantable penile prosthetic system 202, and instructions for use of the tool 100. The implantable penile prosthetic system 202 includes a pump 210 connectable between a reservoir 212 and two prosthetic cylinders 214. The pump 210 operates to move liquid from the reservoir 212 into the inflatable cylinders 214. The inflated cylinders 214, when implanted, provide the penis with an erection. The inflatable cylinders 214 can be deflated by evacuating the air and the liquid from the cylinders, which collapses the cylinders 214 into a flat, pancake shape.

Figure 7:
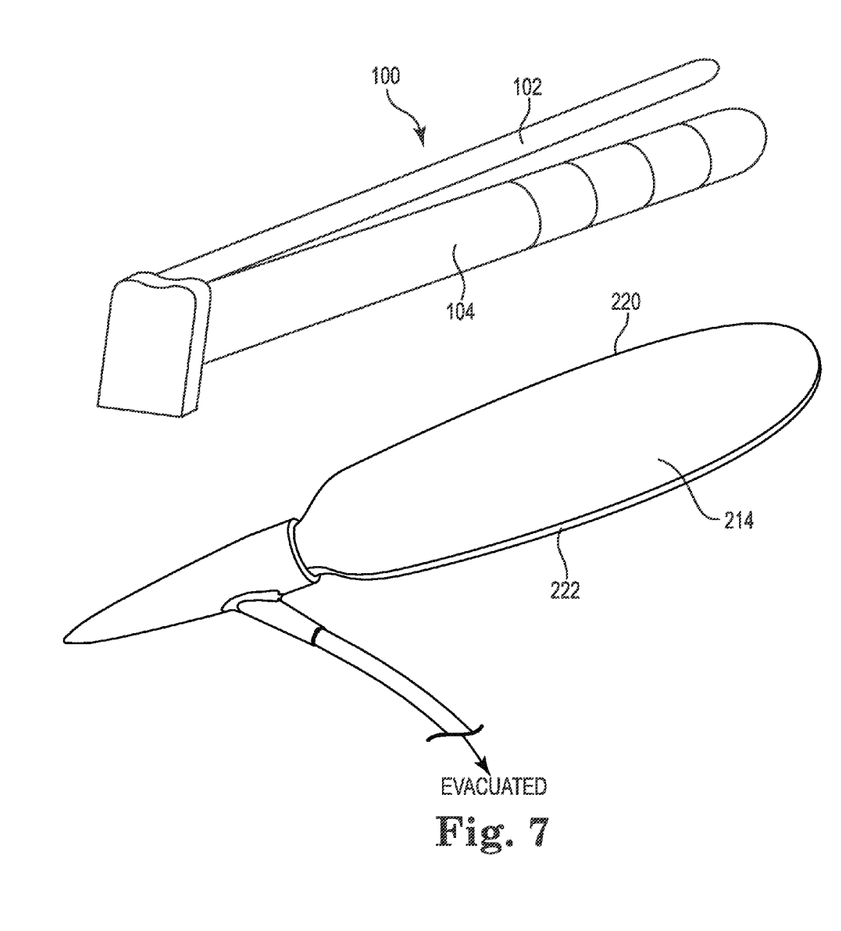
FIG. 7 is a perspective view of the tool illustrated in FIG. 2 and a deflated prosthetic cylinder.

FIG. 7 is a perspective view of one of the deflated cylinders 214 positioned to be secured to the tool 100. The deflated cylinder 214 has a width that extends between a first deflated edge 220 and a second deflated edge 222. The width between the deflated edges 220, 222 is in a range from about 1-4 cm. The deflated edges 220, 222 are wrapped around the curved exterior perimeter 152 of the barrel 104 and inserted under the clasp 102. When deflated, the cylinder has a thickness of about 0.040 inches.

Figure 8A:
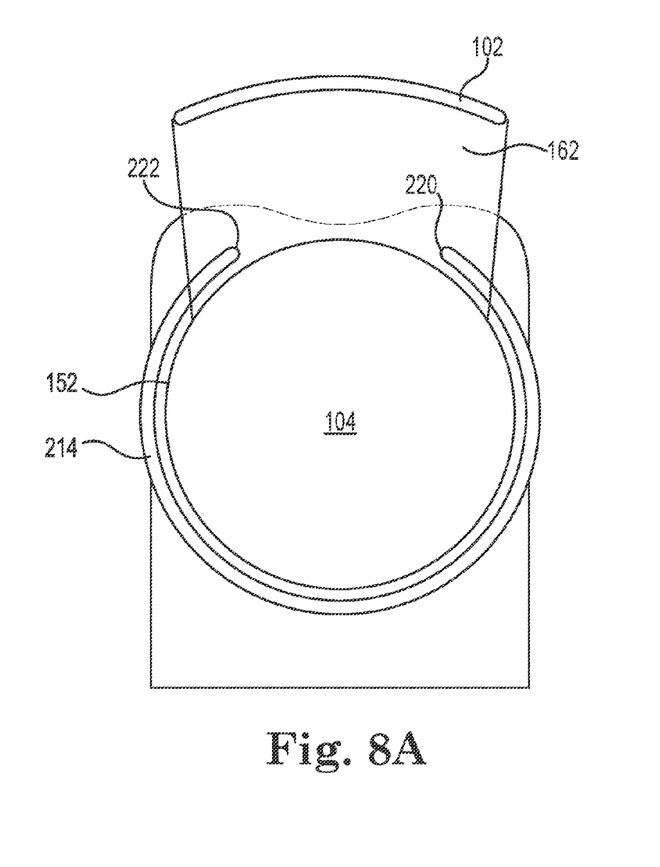
FIGS. 8A and 8B are cross-sectional views of the deflated prosthetic cylinder illustrated in FIG. 7 securely clasped to the barrel of the tool.
Figure 8B:
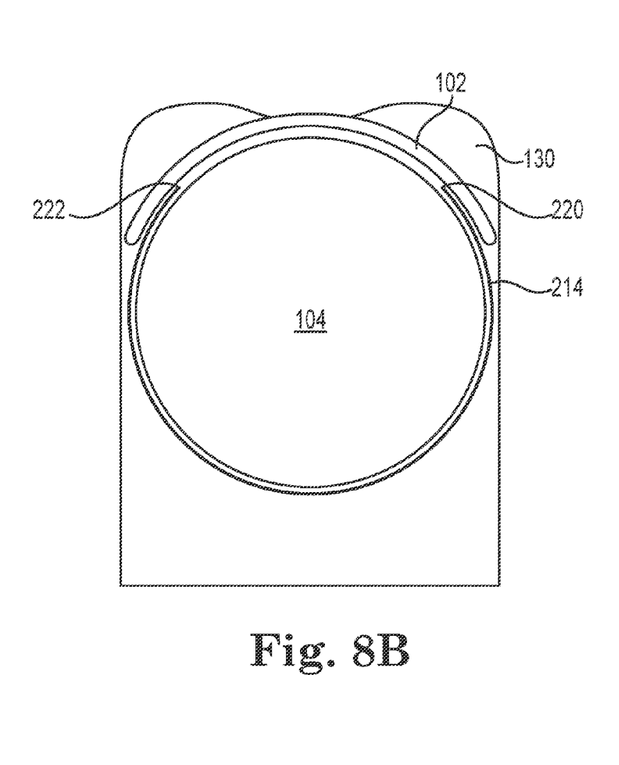

FIG. 8A is an end view of the tool and the deflated cylinder 214 with the clasp 102 elevated away from the barrel 104. FIG. 8B is an end view of the deflated cylinder 214 secured between the clasp 102 and the barrel 104.

The clasp 102 provides a clamping force that captures the deflated edges 220, 222 between the barrel 104 and the clasp 102. With the deflated cylinder 214 secured under the clasp 102, the surgeon inserts the tool 100 and the deflated cylinder 214 into the dilated space formed in one of the corpora cavernosum. The deflated cylinder 214 is delivered through the corpora cavernosum up to the glans penis at which point the surgeon releases the clasp 102 relative to the cylinder 214 and slides the tool 100 away from the inserted cylinder 214. The cylinder 214 slides out from between the clasp 102 and the barrel 104.

Embodiments provide an improved tool for implanting a prosthetic cylinder of an implantable device useful for treating erectile dysfunction. The tool described in this application obviates the use of a Keith needle and does away with perforating the glans penis when implanting a prosthetic cylinder.

Although specific embodiments have been illustrated and described, it will be appreciated by those of ordinary skill in the art that a variety of alternate and equivalent implementations may be substituted for the specific embodiments shown and described without departing from the scope of the present invention. This application is intended to cover any adaptations or variations of the kind of medical devices described above. Therefore, it is intended that this invention be limited only by the claims and their equivalents.

What is claimed is:

1. A method of implanting a penile prosthetic, the method comprising:
   providing a tool having a barrel with a curved exterior perimeter, a clasp having a proximal end that is attached to the tool and a distal end that is free to move away from and towards the barrel, with the clasp having an interior surface located adjacent to the curved exterior perimeter of the barrel;
   deflating an inflatable penile implant to provide a deflated penile implant;
   securing a first lateral edge of the deflated penile implant between the interior surface of the clasp and the curved exterior perimeter of the barrel and securing a second lateral edge of the deflated penile implant between the interior surface of the clasp and the curved exterior perimeter of the barrel;

placing the barrel of the tool and the deflated penile implant into a corpora cavernosum of a penis; and moving the interior surface of the clasp away from the first lateral edge and the second lateral edge of the deflated penile implant, removing the barrel from the corpora cavernosum of the penis, and leaving the deflated penile implant in the corpora cavernosum of the penis.

2. The method of claim 1, further comprising:

securing the first lateral edge of the deflated penile implant in a gap space between the interior surface of the clasp and the curved exterior perimeter of the barrel and securing the second lateral edge of the deflated penile implant in the gap space between the interior surface of the clasp and the curved exterior perimeter of the barrel.

3. The method of claim 1, further comprising:

pressing a pad located on an exterior surface of the clasp and pressing the first lateral edge of the deflated penile implant between the interior surface of the clasp and the curved exterior perimeter of the barrel and pressing the second lateral edge of the deflated penile implant between the interior surface of the clasp and the curved exterior perimeter of the barrel.

4. The method of claim 1, further comprising:

flexing the clasp and moving the distal end of the clasp away from the barrel.

5. The method of claim 1, further comprising:

lifting the clasp and moving the distal end of the clasp away from the barrel.

6. The method of claim 1, further comprising:

dilating the corpora cavernosum of the penis with a dilation tool thus forming a dilated corpora cavernosum of the penis; and directing the barrel of the tool and the deflated penile implant into the dilated corpora cavernosum of the penis.

7. The method of claim 1, further comprising:

pushing against a handle attached to the proximal end of the barrel and moving the barrel of the tool and the deflated penile implant into the corpora cavernosum of the penis.

8. The method of claim 1, further comprising:

pushing the barrel of the tool into the corpora cavernosum of the penis and reading a demarcation located on the barrel and measuring a distal length of the corpora cavernosum of the penis.

9. The method of claim 1, further comprising:

evacuating air form the inflatable penile implant to provide the deflated penile implant.

10. The method of claim 1, further comprising:

evacuating air and liquid form the inflatable penile implant to provide the deflated penile implant.

11. The method of claim 1, further comprising:

implanting a pump into a scrotum;

implanting a reservoir into an abdomen;

coupling the pump to the reservoir and to the inflatable penile implant; and pumping the pump and inflating the inflatable penile implant.

12. A method of implanting a penile prosthetic, the method comprising:

providing a tool having a barrel with an exterior perimeter, a clasp having a proximal end that is attached to the tool and a distal end that is movable away from the barrel, with the clasp having an interior surface located adjacent to the exterior perimeter of the barrel;

deflating an inflatable penile implant to provide a deflated penile implant;

lifting the clasp and moving the distal end of the clasp away from the exterior perimeter of the barrel;

securing a first lateral edge of the deflated penile implant between the interior surface of the clasp and the exterior perimeter of the barrel;

securing a second lateral edge of the deflated penile implant between the interior surface of the clasp and the exterior perimeter of the barrel;

placing the barrel of the tool and the deflated penile implant into a corpora cavernosum of a penis; and moving the interior surface of the clasp away from the first lateral edge and the second lateral edge of the deflated penile implant and withdrawing the barrel from the corpora cavernosum of the penis.

13. The method of claim 12, further comprising:

pressing on an exterior surface of the clasp and pressing the first lateral edge of the deflated penile implant between the interior surface of the clasp and the exterior perimeter of the barrel and pressing the second lateral edge of the deflated penile implant between the interior surface of the clasp and the exterior perimeter of the barrel.

\* \* \* \* \*